(12) United States Patent
Leconte et al.

(10) Patent No.: US 9,518,937 B2
(45) Date of Patent: Dec. 13, 2016

(54) OPTICAL METHOD FOR INSPECTING TRANSPARENT OR TRANSLUCENT ARTICLES INTENDED TO ALLOCATE A REFERENCE OPTICAL ADJUSTMENT TO THE VISION SYSTEM

(71) Applicant: MSC & SGCC, Vourles (FR)

(72) Inventors: Marc Leconte, Loire sur Rhone (FR); Bernard Lopez, Lyons (FR)

(73) Assignee: MSC & SGCC, Vourles (FR)

( * ) Notice: Subject to any disclaimer, the term of this patent is extended or adjusted under 35 U.S.C. 154(b) by 317 days.

(21) Appl. No.: 14/373,410

(22) PCT Filed: Jan. 25, 2013

(86) PCT No.: PCT/FR2013/050157
§ 371 (c)(1),
(2) Date: Jul. 21, 2014

(87) PCT Pub. No.: WO2013/110899
PCT Pub. Date: Aug. 1, 2013

(65) Prior Publication Data
US 2014/0362207 A1    Dec. 11, 2014

(30) Foreign Application Priority Data

Jan. 27, 2012    (FR) .................................. 12 50820

(51) Int. Cl.
*G01N 21/958*    (2006.01)
*G01N 21/90*    (2006.01)
(Continued)

(52) U.S. Cl.
CPC ............ *G01N 21/958* (2013.01); *G01N 21/41* (2013.01); *G01N 21/90* (2013.01);
(Continued)

(58) Field of Classification Search
CPC .................................................... G01N 21/958
See application file for complete search history.

(56) References Cited

U.S. PATENT DOCUMENTS

| 4,606,634 A | 8/1986 | Bieringer |
| 4,636,073 A * | 1/1987 | Williams ............... G01N 21/94 356/237.5 |

(Continued)

FOREIGN PATENT DOCUMENTS

DE    199 46 080    5/2000

*Primary Examiner* — James Pontius
(74) *Attorney, Agent, or Firm* — Clark & Brody

(57) ABSTRACT

A method of inspecting articles of transparent/translucent material with a vision system comprises illuminating the articles with a light source having an angular spectrum that is adapted to the contrast selected for refractive items presented by the articles. An image sensor picks up the light that has passed through the articles to make images of the articles. During a stage of referencing the vision system, a reference standard is in the field of view of the image sensor, the standard including at least one standard item that refracts light in a known range of angles. An image of the standard is taken to measure at least the contrast in the image produced by at least one standard item. During at least one stage of qualifying the vision system, the standard is placed once more in front of the light source and in the field of view of the image sensor.

17 Claims, 3 Drawing Sheets

(51) Int. Cl.
*G01N 21/93* (2006.01)
*G01N 21/41* (2006.01)
*H04N 5/232* (2006.01)
*H04N 5/235* (2006.01)

(52) U.S. Cl.
CPC ......... *G01N 21/9045* (2013.01); *G01N 21/93* (2013.01); *H04N 5/2354* (2013.01); *H04N 5/23238* (2013.01)

(56) References Cited

U.S. PATENT DOCUMENTS

| | | | |
|---|---|---|---|
| 6,137,893 A * | 10/2000 | Michael | G06T 7/0018 348/87 |
| 7,599,051 B1 | 10/2009 | Labovitz et al. | |
| 2012/0211638 A1 * | 8/2012 | Yoshida | H04N 5/23212 250/201.2 |

* cited by examiner

OPTICAL METHOD FOR INSPECTING TRANSPARENT OR TRANSLUCENT ARTICLES INTENDED TO ALLOCATE A REFERENCE OPTICAL ADJUSTMENT TO THE VISION SYSTEM

The present invention relates to the technical field of optically inspecting translucent or transparent articles in order to detect any light-absorbing and/or light-refracting items presented by such articles.

A particularly advantageous application for the invention lies in detecting as light-absorbing and/or light-refracting items any defects that appear in articles such as containers made of glass or of plastics material.

Another particularly advantageous application of the invention lies in detecting and identifying as light-absorbing and/or light-refracting items a mark or an engraving containing information, e.g. encoding a mold number.

It is known to perform automatic and in-line inspection of articles such as containers traveling at a high rate past an optical control station having a vision system comprising a light source situated on one side of the container and a camera situated on the other side of the container. The camera takes an image using light that passes through the containers. This type of illumination is said to be by transmission. Naturally, a plurality of inspection stations are needed in order to inspect all of the containers. It is thus known to make use of equipment comprising eight to twenty-four cameras for inspecting the vertical walls of the containers. In order to inspect the bottoms of the containers, other equipment is provided where the camera is situated above the container and the light source under the bottom of the container. An image of the bottom of the container is taken through the neck of the container.

In general, the light source is uniform and extensive compared with the inspected article. When observing under such conditions, the defects in such articles behave differently depending on their natures and on their shapes and they may be classified in two categories. Certain defects such as inclusions of material or of non-transparent dirt absorb light, whereas, more rarely, folds or strongly marked surface roughnesses refract light strongly. Under such observation conditions, these defects present contrast in the image that is sufficient to enable them to be detected.

Other refracting defects that are less marked, such as bubbles of air, surface folds, or local variations in the thickness of the transparent material give rise, under these observation conditions to contrast in the image that is not sufficient to enable them to be detected. This applies in particular to emerging spikes of glass.

When inspecting the bottoms of containers, it is known to detect as soon as possible the emergence of a spike of glass since this is a defect that is critical and dangerous, and it emerges progressively during the production of containers. The spike of glass appears initially as a small bulge of glass on the bottom of the container and it becomes more marked progressively.

On the same lines, detecting and then identifying engraving requires the shape of the engraving to appear in full with sufficient contrast in the image, and this does not happen with purely diffusing uniform light sources.

In order to detect refracting items such as engraving or defects, proposals are made in the state of the art, e.g. in U.S. Pat. No. 4,606,634, to use a source that enhances the contrast of refractive items. The light source comprises a source that is extensive, uniform, and diffusing, with an interchangeable mask or an iris diaphragm being placed thereon to define the aperture of said source. This produces a source that is uniform, plane, and diffuse, referred to as a primary source, which source has the feature of being of variable size. A converging lens is positioned above the primary source, e.g. a Fresnel type lens, and its focus is preferably situated on the primary light source, i.e. its focal length is preferably equal to the distance between the lens and the primary source. As explained in U.S. Pat. No. 4,606,634, the light source illuminates the entire field defined by the lens by means of light rays presenting an angular spectrum that depends directly on the size of the primary source, in other words on the aperture of the diaphragm or the mask of the source. Consequently, the contrast on refractive items observed in transmission is adjusted by adjusting the aperture of the mask or the diaphragm of the light source.

It should be observed that when there is a change in the articles that are to be inspected, the vision system needs to be adjusted so as to enable light-refracting items to be detected. Furthermore, such an adjustment of the vision system is also found to be necessary when detection is found to drift over time. Unfortunately, it is particularly difficult in practice to adjust such a vision system in order to detect light-refracting items with a given level of detection. This difficulty stems in particular from the number of parameters that can be adjusted, from the way they are interdependent, and from the way these parameters vary over time. Additionally, when a plurality of pieces of equipment are used in parallel to inspect streams of identical articles, it is desirable for each piece of equipment to perform inspection at the same level. Unfortunately, it is found difficult or even impossible in practice to obtain a reproducible adjustment level on the vision systems that form parts of a plurality of pieces of inspection equipment, not only for the reasons mentioned above, but also because of the variable nature of the components making up such vision systems.

The present invention thus seeks to remedy the drawbacks of the prior art by proposing a method that makes it easy to adjust in reproducible manner a vision system for detecting, with a given level of detection, light-refracting items such as defects, marks, or engraving.

To achieve this object, the invention provides an optical method of inspecting articles of transparent or translucent material with the help of a vision system. The method of the invention consists:
  in illuminating the articles with the help of a light source having an angular spectrum that is adapted to the contrast selected for refractive items presented by the articles;
  in using an image sensor for picking up the light that has passed through the articles in order to make images of the articles; and
  in analyzing the images in order to detect the presence of light-refracting items.
  According to the invention, the method consists:
  during a stage of referencing the vision system:
    in placing a reference standard in front of the light source and in the field of view of the image sensor, the reference standard including at least one standard item that refracts light in a known range of angles; and
    in taking at least one image of the reference standard so as to measure at least the contrast in the image produced by at least one standard item and corresponding to an optimized optical adjustment of the vision system; and
  during at least one stage of qualifying the vision system:

in placing the reference standard once more in front of the light source and in the field of view of the image sensor;

in taking at least one image of the reference standard so as to measure at least the contrast in the image produced by the standard item and corresponding to the optical adjustment of the vision system during this qualification stage; and in determining at least whether the contrast in the image produced by the standard item corresponding to the optical adjustment of the vision system during this qualification stage does or does not comply with the contrast in the image produced by the standard item during the referencing stage.

Furthermore, the method of the invention may also include in combination at least one or more of the following additional characteristics:

during the qualification stage for adjusting a vision system, optically adjusting the vision system so that the contrast in the image produced by the standard item corresponding to said adjustment is in compliance with the contrast in the image produced by the standard item during the referencing stage;

during the qualification stage seeking to verify the optical adjustment of the vision system, comparing the contrast in the image produced by the standard item during the referencing stage with the contrast of the image produced by the standard item during this qualification stage, in order to determine whether the optical adjustment of the vision system has changed, and if it has changed, issuing a warning and/or adjusting the vision system in such a manner that the contrast in the image produced by the standard item during this referencing stage complies with the contrast in the image produced by the standard item during the referencing stage;

during the stage of referencing the vision system, performing an adjustment pre-step prior to positioning the reference standard, which adjustment pre-step consists in placing a reference article in front of the light source and in the field of view of the image sensor, and in adjusting the vision system to obtain an optimized optical adjustment;

while taking images, storing either the image of the reference standard, or at least measuring said contrast in the image produced by the standard item and corresponding to the optical adjustment of the vision system;

measuring the contrast in the image of the standard items either by the area or by the width of the dark portion of the image of the standard item, or by the ratio between the area of the dark portion of the image of the standard item to the total area of the image of the standard item, or by the area or the diameter of the pale portion of the image of the refracting standard item, or by the ratio of the area of the pale portion of the image of the standard item to the total area of the image of the standard item, or by the histogram of the image of the standard item, or by the mean gray level of the standard item;

in addition to measuring the contrast of the standard items, measuring in the image the mean brightness of the image, and/or the sharpness, and/or the magnification, and/or the brightness of graded density filters;

placing a reference standard in front of the light source, the reference standard having a plurality of standard items that refract light in different known angle ranges;

placing the reference standard in front of the light source, the reference standard including graded density filters and/or a range of opaque items of known dimensions;

providing as light-refracting standard items, lenses, transparent cones, or transparent dihedral ridges; and making the light-refracting standard items out of a material that presents a refractive index that is substantially equal to the refractive index of the material of the articles.

The invention also proposes a reference standard for performing the optical inspection method in accordance with the invention and comprising a medium provided with a series of standard items that refract light in different known angle ranges.

In addition, the reference standard of the invention may also include in combination at least one or more of the following additional characteristics:

as standard items, lenses, transparent cones, or transparent dihedral ridges;

a series of graded density filters; and a series of opaque zones of different dimensions.

The invention also proposes an optical inspection station for inspecting articles with the help of a vision system, the station including a support for a reference standard in accordance with the invention, and a system for moving the support in order to place the reference standard temporarily in the field of view of the image sensor so that it takes the place of an article.

In another variant embodiment, the optical station of the invention includes a system enabling at least one parameter that influences the optical adjustment of the vision system to be controlled automatically, the system itself being controlled by the unit for processing and analyzing images from the vision system so as to act on at least one parameter that influences the optical adjustment of the vision system in such a manner that the contrast in the image produced by the standard item corresponding to the optical adjustment of the vision system during the qualification stage complies with the contrast in the image produced by the standard item during the referencing stage.

Various other characteristics appear from the following description made with reference to the accompanying drawings, which show embodiments of the invention as non-limiting examples.

Figure 1:
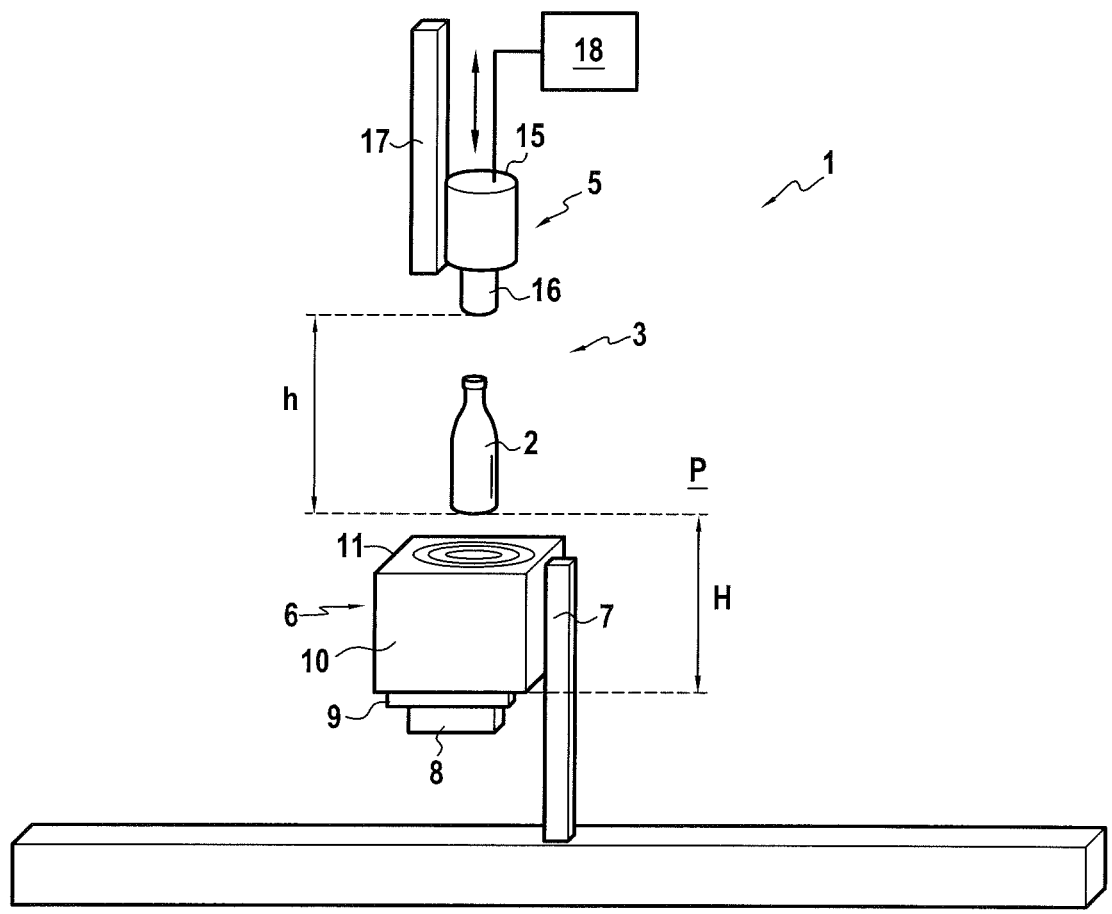
FIG. 1 is a diagrammatic view for explaining the method of using a vision system for inspecting items that absorb and/or refract light.

By way of example, FIG. 1 shows an optical inspection station 1 for articles 2 made of transparent or translucent material such as containers in the example shown. Containers 2 are inspected optically with the help of a vision system 3. In conventional manner, the containers 2 are conveyed in succession past the vision system 3 by any suitable conventional means, while they are positioned in a reference plane P.

The vision system 3 has an image sensor 5 and a light source 6 illuminating the containers 2. In the example shown, the light source 6 is placed under the bottom of the container 2 while the image sensor 5 is placed above the neck of the container 2. In this configuration, an image of the bottom of the container 2 is taken through the neck of the container 2 in order to detect light refracting items situated in the bottom of the container. Naturally, provision may be made for the vision system 3 to inspect the vertical walls of the containers 2. Under such circumstances, the image sensor 5 and the light source 6 are placed on either side of the vertical walls of the container 2.

The light source 6 is designed to enhance the contrast of light refracting objects such as defects of the glass spike type for example. The light source 6 thus presents the characteristics of the light source described in U.S. Pat. No. 4,606,634.

The light source 6 delivers a light beam of angular spectrum that is adapted to the contrast selected or desired for the refracting items presented by the container 2. In conventional manner, the light source 6 is mounted on a support 7 with the possibility of adjustment enabling the position of the light source 6 to be adjusted relative to the reference plane P. The light source 6 comprises a source of illumination 8, e.g. constituted by a series of light-emitting diodes (LEDs) that are switched on for a duration that is controlled by a control circuit that is not shown, but that is itself known.

The light source 6 also has a diaphragm 9 of adjustable nature for adjusting the aperture of the source of illumination 8.

This produces a uniform source that is plane and diffuse presenting a variable dimension and delivering light flux that is conveyed to the inside of a block 10 provided with a converging lens 11, e.g. of the Fresnel type. The converging lens 11 is placed in such a manner that its focus is situated substantially on the diaphragm 9, i.e. the focal length of the lens 11 is equal to the distance between the lens and the diaphragm 9. As explained in U.S. Pat. No. 4,606,634, the light source 6 illuminates all of the field defined by the lens 11 with the help of light rays presenting an angular spectrum that depends directly on the aperture of the diaphragm 9. Thus, the contrast on refractive items observed in transmission is adjusted by the aperture of the diaphragm 9.

The light that has passed through the container 2 is picked up with the help of the image sensor 5 and serves to constitute one or more images of the container 2. The image sensor 5 includes a camera 15 with an objective lens 16. Advantageously, the image sensor 5 is adjustably mounted on a support 17 enabling the distance or the height h of the image sensor 5 relative to the reference plane P to be adjusted. The image sensor 5 is connected to a unit 18 for processing and analyzing the images taken and serving in particular to detect the presence of light-refracting items in the articles 2.

The way articles 2 are inspected with the help of the vision system 3 stems directly from the above description. For this purpose, the inspection method consists:

in illuminating the articles 2 with the help of the light source 6 with its angular spectrum adapted to the contrast selected for the refractive items presented by the articles 2 and that it is desired to detect;

in using the image sensor 5 to pick up the light that has passed through the articles 2 in order to constitute images of the articles 2; and in analyzing the images in order to detect the presence of light-refracting items, if any.

The vision system 3 is adjusted so as to detect the presence of refractive items in the container 2. The optical adjustment of the vision system 3 corresponds to the configuration of various elements making up the vision system 3, namely the camera 15, its lens 16, and the light source 6. The optical adjustment of the vision system 3 thus determines the configuration of all of the optical, mechanical, electronic, or digital parameters that influence the brightness, the contrast, and the resolution of the image. The parameters that influence the optical adjustment of the vision system 3 are as follows:

the gain of the camera 15 that is applied to the brightness and that presents a value that is fixed;

the integration time of the camera 15 that applies to the brightness and that may be subjected to adjustment;

an aperture of the objective lens 16 that acts on the brightness and on the depth of field;

the focal length of the objective lens 16 that is adjustable and that acts on the magnification of the image;

the focusing of the objective lens 16;

the height h of the camera 15 relative to the reference plane P, acting on the size of the image, this height h being adjustable relative to the reference plane P;

the height H of the light source 6 relative to the reference plane P, which is capable of being adjusted and which acts on contrast;

the diaphragm 9 of the light source 6 that is capable of being adjusted and that acts on the contrast of refractive items in the image; and the length of time the light source 6 delivers light, which is capable of being adjusted and which acts on the brightness of the image.

The invention seeks to propose a simple method for adjusting the vision system 3 or for verifying the optical adjustment of the vision system 3, such a vision system 3 presenting optical adjustment that is optimized to detect any light-refracting items that might be presented by the articles 2. In accordance with the invention, the method of adjusting or verifying the optical adjustment of the vision system 3 consists in using a reference standard 20.

Figure 2:
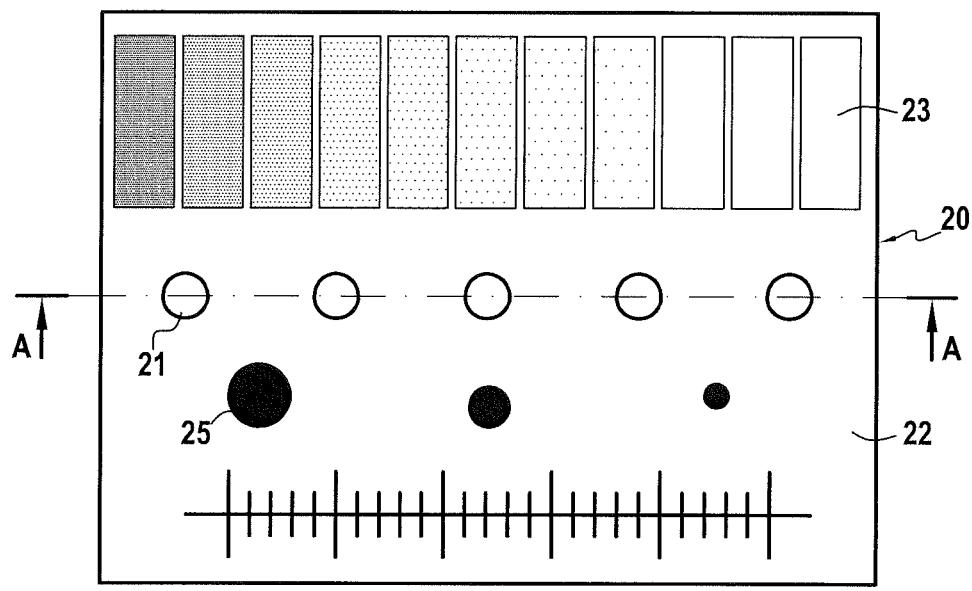
FIG. 2 shows an embodiment of a reference standard used for performing the method in accordance with the invention.
Figure 2A:
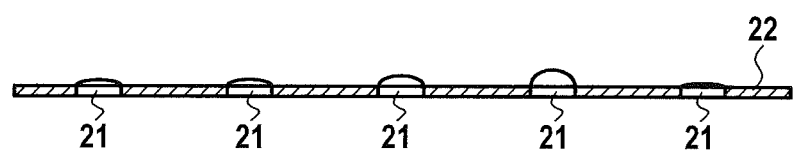
FIG. 2A is a section view of the reference standard taken substantially on line A-A of FIG. 2.
Figure 3:
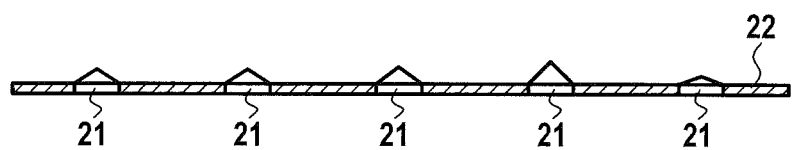
FIG. 3 is a section view of another embodiment of a reference standard having transparent cones as its standard items.
Figure 4:
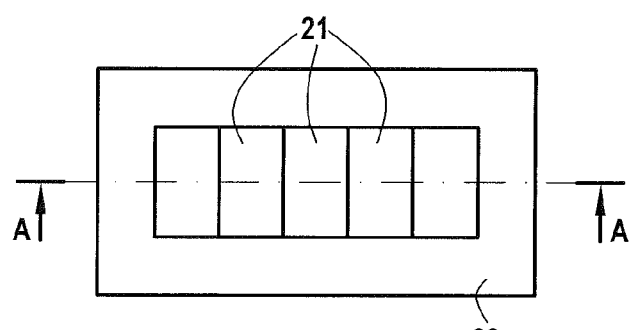
FIGS. 4 and 4A are respectively a plan view and a section view on line A-A of FIG. 4 showing another embodiment of a reference standard having transparent dihedral ridges as standard items.
Figure 4A:
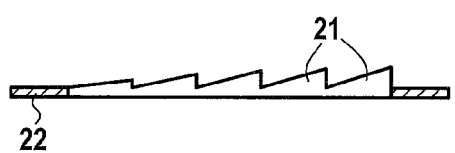

As can be seen more clearly in the embodiment shown in FIGS. 2 and 2A, the reference standard 20 has at least one (and in the example shown five) standard items 21 that refract light in a known range of angles. In the example shown in FIGS. 2 and 2A, the reference standard 20 comprises a medium 22 such as a metal plate having holes, or a plastics plate, on which standard items 21 are mounted in the form of plano-convex transparent lenses. In the example shown, the five plano-convex lenses 21 have a diameter of 5 millimeters (mm) and respective focal lengths equal to 5 mm, 7.5 mm, 10 mm, 12 mm, and 15 mm. Naturally, it is clear that the reference standard could present some other number of standard items 21 with different focal lengths. The standard items 21 are mounted on the medium 22 so as to be capable of being placed simultaneously in the field of view of the camera 15. It should be observed that the standard items 21 may be made of transparent material with some other geometrical configuration. For example, the standard items 21 may be made as transparent cones (FIG. 3) or as transparent dihedral ridges (FIGS. 4 and 4A), and they may present a range of angles of refraction, these standard items 21 being obtained by molding and/or machining and/or by polishing. In the example shown in the drawings, the standard items 21 are projecting optical elements, however it is clear that these optical elements could be recessed. Likewise, FIGS. 2 and 2A show plano-convex lenses as standard items 21, however it is clear that a standard item 21 could be in the form of a plano-convex lens, a biconcave lens, or a biconvex lens.

According to an advantageous characteristic of the invention, the standard items 21 are made of a material presenting a refractive index that is substantially equal to the refractive index of the containers 2.

The reference standard 20 as described above is used for adjusting the vision system 3 or for verifying the adjustment of the vision system 3. This "calibration" procedure comprises two stages:
  a first stage of referencing the vision system 3 during which the optical adjustment of the vision system is characterized; and
  a second stage of qualifying the vision system 3 serving to adjust or to verify the optical adjustment of the vision system 3.

This second stage of qualification takes place in time after the first stage of referencing and it may naturally be repeated at will in order to verify the stability of the optical adjustment of the vision system 3 over time, with verification optionally being performed on a regular basis.

Figure 5:
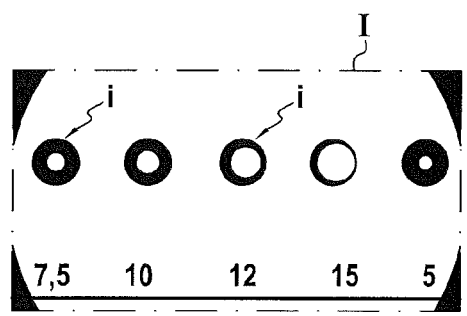
FIG. 5 is an image I of the reference standard for a given optical adjustment of the vision system in accordance with the invention.
Figure 6:
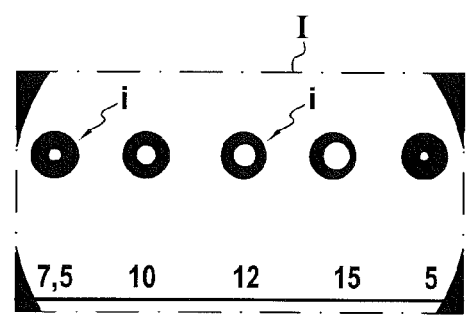
FIG. 6 is another image I of the reference standard for another optical adjustment of the vision system in accordance with the invention.

The calibration procedure is thus performed when adjusting the vision system 3 for a new production of containers 2 or when verifying the optical adjustment of the vision system 3. During this calibration procedure, no container 2 is placed in the field of view of the image sensor 5. The referencing stage of the vision system 3 consists:
  in placing the reference standard 20 in front of the light source 6 and in the field of view of the image sensor 5; and
  in taking at least one image I of the reference standard 20 so as to measure at least one reference optical characteristic corresponding to an optimized optical adjustment of the vision system 3. FIG. 5 shows an image I taken with the reference standard 20 located in the place of a container 2. This image I has five images i of the standard items 21 of the reference standard 20. As can be seen clearly in FIG. 5, the refraction of light by each standard item 21 leads to an image i of the standard item 21 that has a dark portion and a pale portion. FIG. 6 shows another image I of the reference standard 20 as obtained with a different optical adjustment of the vision system 3.

The image I of the reference standard is analyzed in order to quantify or measure at least one reference optical characteristic corresponding to the optical adjustment of the vision system 3. As an optical adjustment characteristic of the vision system 3, account is taken at least of the contrast in the image produced by light being refracted by at least one and generally all of the standard items 21.

Contrast may be measured in the image of the standard items 21 in various ways, such as, for example:
  by measuring the area or the width of the dark portion of the image i of the standard item 21;
  as the ratio between the measured area of the dark portion of the image i of the standard item 21 and the measured total area of the image i of the standard item 21;
  by measuring the area or the width of the pale portion of the image i of the standard item 21;
  as the ratio between the measured area of the pale portion of the image i of the standard item 21 to the measured total area of the image i of the standard item 21;
  by the mean gray level of the standard item 21; and/or
  by the histogram of the image i of the standard item 21.

It is clear that it is possible to adapt the above measurements as a function of the geometrical configuration of the standard items 21 used, such as for example transparent cones or transparent dihedral ridges.

It should be understood that this stage of referencing the vision system 3 makes it possible to characterize an optical configuration not by taking account of all of the parameters that influence the optical adjustment, some of which are difficult to measure, but rather by relying on its looked-for effect concerning the detection of refractive defects. For this purpose, characterization may be transposed in time and from one machine to another, and this applies in spite of the dispersion of the physical characteristics of the machines. This characterization of the optical adjustment of the vision system 3 is performed by measuring at least one reference optical characteristic corresponding to one and/or another of the contrast measurements in the image of the standard items 21.

In an advantageous implementation characteristic, the method consists in storing either the image I of the reference standard 20 or at least in measuring characteristics of the optical adjustment of the vision system 3, i.e. one and/or another of the contrast measurements in the image of the standard items 21 as described above.

After completing the referencing stage, the calibration procedure seeks to perform the stage of qualifying the vision system 3, which stage consists either in verifying the optical adjustment of the vision system or in adjusting the vision system.

The qualification stage is performed while no container 2 is in place in the field of view of the camera 15.

When this qualification stage seeks to verify the stability of the optical adjustment of the vision system 3, this qualification stage consists:
  in placing the reference standard 20 once more in front of the light source 6 and in the field of view of the image sensor 5;
  in taking at least one image I of the reference standard 20 so as to measure at least one optical characteristic corresponding to the optical adjustment of the vision system 3 during this qualification stage; and
  in determining whether the optical characteristic corresponding to the optical adjustment of the vision system 3 during this qualification stage does or does not comply with the reference optical characteristic as determined during the stage of referencing the vision system 3.

As explained above with reference to the referencing stage, the method of the invention seeks in this qualification stage to take account, as a characteristic of the optical adjustment of the vision system 3, of at least the contrast in the image produced by light being refracted by the standard items 21.

The method thus consists in comparing the reference optical characteristic and the optical characteristic corresponding to the optical adjustment of the vision system 3 during this qualification stage in order to determine whether the optical adjustment of the vision system 3 has changed. In other words, the method of the invention consists in comparing the contrast in the image produced by the standard items 21 during the referencing stage and during the qualification stage.

If it is found that the optical characteristic corresponding to the optical adjustment of the vision system 3 during this qualification stage corresponds to the reference optical characteristic, then the calibration procedure is terminated and it is possible to continue with the method of inspecting articles 2.

If it is found that the optical characteristic corresponding to the optical adjustment of the vision system 3 during this qualification stage does not correspond to the reference optical characteristic, then the method consists in issuing a warning signal and/or in adjusting the vision system 3 so that the optical characteristic corresponding to the optical adjustment complies with the reference optical characteristic. Naturally, the vision system 3 is adjusted using one and/or another of the above-mentioned parameters of the vision system.

It should be observed that the stage of qualifying a vision system 3 may be used for the purpose of optically adjusting the vision system 3. Under such circumstances, the vision system 3 is optically adjusted so that the optical characteristic corresponding to said adjustment complies with the reference optical characteristic. Naturally, the vision system 3 is adjusted using one and/or another of the above-mentioned parameters of the vision system 3.

It should be observed that such a stage seeking to adjust a vision system may be performed with the help of a vision system that is identical to or different from the vision system used during the referencing stage. This possibility makes it possible to adjust in identical manner two vision systems that may, for example, be located in parallel for inspecting a production of articles 2. Thus, after adjusting the first vision system using the calibration procedure as described above, the calibration procedure for the second vision system consists in comparing the optical characteristic corresponding to the adjustment of the second vision system 3 with the reference optical characteristic determined during the referencing stage and stored in the processor unit associated with the second vision system. Storage in the processor unit associated with the second vision system may be achieved in any appropriate manner, e.g. by transmission from the first vision system or by using a removable storage medium. The second vision system is adjusted so that the optical characteristic corresponding to the adjustment of the second vision system complies with the reference optical characteristic.

It should be observed that it may be advantageous during the stage of referencing the vision system to begin, prior to positioning the reference standard 20, with an adjustment pre-step consisting in placing a standard or reference container in front of the light source 6 and in the field of view of the image sensor 5, and in adjusting the vision system 3 in order to obtain an optimized optical adjustment.

In an advantageous variant implementation, the reference standard 20 also includes filters 23 of graded density suitable for accentuating the brightness of the image. In another preferred variant implementation, the reference standard 20 also includes a range of opaque items 25 of known dimensions, such as spots of different diameters, making it possible to verify the sharpness and/or the magnification of the vision system 3.

From the above description, it can be seen that performing the invention consists in placing the reference standard 20 in the field of view of the camera instead of an article 2. In an advantageous variant implementation, the optical inspection station 1 may include a support (not shown) for supporting the reference standard 20 and a manual or motor-driven movement system enabling the reference support to be placed temporarily in the field of view of the image sensor, instead of an article 2.

In an advantageous variant implementation, the optical inspection station 1 includes a system enabling at least one parameter that has an influence on the optical adjustment of the vision system 3 to be controlled automatically, the system itself being controlled by the unit 18 for processing and analyzing images from the vision system 3 so as to act on at least one parameter having an influence on the optical adjustment of the vision system 3 in order to ensure that the contrast in the image produced by the standard item 21 corresponding to the optical adjustment of the vision system 3 as performed during the qualification stage does indeed comply with the contrast in the image produced by the standard item 21 during the referencing stage.

The invention is not restricted to the examples described and shown, since various modifications may be applied thereto without going beyond its ambit.

The invention claimed is:

1. An optical method of inspecting articles (2) of transparent or translucent material with the help of a vision system (3), the method consisting:

in illuminating the articles (2) with the help of a light source (6) having an angular spectrum that is adapted to the contrast selected for refractive items presented by the articles (2);

in using an image sensor (5) for picking up the light that has passed through the articles (2) in order to make images of the articles (2); and in analyzing the images in order to detect the presence of light-refracting items;

the method being characterized in that it consists:

during a stage of referencing the vision system (3):

in placing a reference standard (20) in front of the light source (6) and in the field of view of the image sensor (5), the reference standard (20) including at least one standard item (21) that refracts light in a known range of angles; and in taking at least one image of the reference standard (20) so as to measure at least the contrast in the image produced by at least one standard item (21) and corresponding to an optimized optical adjustment of the vision system (3); and during at least one stage of qualifying the vision system (3):

in placing the reference standard (20) once more in front of the light source (6) and in the field of view of the image sensor (5);

in taking at least one image (I) of the reference standard (20) so as to measure at least the contrast in the image produced by the standard item (21) and corresponding to the optical adjustment of the vision system (3) during this qualification stage; and in determining at least whether the contrast in the image produced by the standard item (21) corresponding to the optical adjustment of the vision system (3) during this qualification stage does or does not comply with the contrast in the image produced by the standard item (21) during the referencing stage.

2. A method according to claim 1, characterized in that, during the qualification stage for adjusting a vision system (3), it consists in optically adjusting the vision system (3) so that the contrast in the image produced by the standard item (21) corresponding to said adjustment is in compliance with the contrast in the image produced by the standard item (21) during the referencing stage.

3. A method according to claim 1, characterized in that, during the qualification stage seeking to verify the optical adjustment of the vision system (3), it consists in comparing the contrast in the image produced by the standard item (21) during the referencing stage with the contrast of the image produced by the standard item (21) during this qualification stage, in order to determine whether the optical adjustment of the vision system (3) has changed, and if it has changed, in issuing a warning and/or in adjusting the vision system (3) in such a manner that the contrast in the image produced by the standard item (21) during this referencing stage complies with the contrast in the image produced by the standard item (21) during the referencing stage.

4. A method according to claim 1, characterized in that, during the stage of referencing the vision system (3), it consists in performing an adjustment pre-step prior to positioning the reference standard (20), which adjustment pre-step consists in placing a reference article in front of the light source (6) and in the field of view of the image sensor (5), and in adjusting the vision system (3) to obtain an optimized optical adjustment.

5. A method according to claim 1, characterized in that, while taking images, it consists in storing either the image of the reference standard (20), or at least measuring said contrast in the image produced by the standard item (21) and corresponding to the optical adjustment of the vision system (3).

6. A method according to claim 2, characterized in that it consists in measuring the contrast in the image of the standard items (21) either by the area or by the width of the dark portion of the image (i) of the standard item (21), or by the ratio between the area of the dark portion of the image (i) of the standard item (21) to the total area of the image (i) of the standard item (21), or by the area or the diameter of the pale portion of the image (i) of the refracting standard item (21), or by the ratio of the area of the pale portion of the image (i) of the standard item (21) to the total area of the image (i) of the standard item (21), or by the histogram of the image (i) of the standard item (21), or by the mean gray level of the standard item.

7. A method according to claim 1, characterized in that it consists, in addition to measuring the contrast of the standard items (21), in measuring in the image the mean brightness of the image, and/or the sharpness, and/or the magnification, and/or the brightness of graded density filters.

8. A method according to claim 1, characterized in that it consists in placing a reference standard (20) in front of the light source (6), the reference standard having a plurality of standard items (21) that refract light in different known angle ranges.

9. A method according to claim 1, characterized in that it consists in placing the reference standard (20) in front of the light source (6), the reference standard including graded density filters (23) and/or a range of opaque items (25) of known dimensions.

10. A method according to claim 1, characterized in that it consists in providing as light-refracting standard items (21), lenses, transparent cones, or transparent dihedral ridges.

11. A method according to claim 1, characterized in that it consists in making the light-refracting standard items (21) out of a material that presents a refractive index that is substantially equal to the refractive index of the material of the articles (2).

12. A reference standard for performing the optical inspection method in accordance with claim 1, the standard being characterized in that it comprises a medium (22) provided with a series of standard items (21) that refract light in different known angle ranges.

13. A reference standard according to claim 12, characterized in that, as standard items (21) it includes lenses, transparent cones, or transparent dihedral ridges.

14. A reference standard according to claim 12, characterized in that it includes a series of graded density filters (23).

15. A reference standard according to claim 12, characterized in that it includes a series of opaque zones (25) of different dimensions.

16. An optical inspection station for inspecting articles (2) with the help of a vision system (3), the station being characterized in that it includes a support for a reference standard (20) according to claim 12, and a system for moving the support in order to place the reference standard (20) temporarily in the field of view of the image sensor so that it takes the place of an article (2).

17. An optical inspection station according to claim 16, characterized in that it includes a system enabling at least one parameter that influences the optical adjustment of the vision system (3) to be controlled automatically, the system itself being controlled by the unit (18) for processing and analyzing images from the vision system (3) so as to act on at least one parameter that influences the optical adjustment of the vision system (3) in such a manner that the contrast in the image produced by the standard item (21) corresponding to the optical adjustment of the vision system (3) during the qualification stage complies with the contrast in the image produced by the standard item (21) during the referencing stage.

* * * * *